United States Patent
Hogard

(10) Patent No.: US 8,926,544 B2
(45) Date of Patent: Jan. 6, 2015

(54) SYSTEM AND METHOD FOR DETECTING ACCESS DISCONNECTION

(75) Inventor: Michael Hogard, Odessa, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 488 days.

(21) Appl. No.: 13/452,447

(22) Filed: Apr. 20, 2012

(65) Prior Publication Data

US 2012/0205312 A1 Aug. 16, 2012

Related U.S. Application Data

(63) Continuation of application No. 12/180,331, filed on Jul. 25, 2008, now Pat. No. 8,192,388.

(51) Int. Cl.
| | |
|---|---|
| A61M 37/00 | (2006.01) |
| A61M 1/36 | (2006.01) |
| B01D 11/00 | (2006.01) |
| B01D 61/00 | (2006.01) |
| C02F 1/44 | (2006.01) |
| A61M 1/10 | (2006.01) |

(52) U.S. Cl.
CPC ........... *A61M 1/3653* (2013.01); *A61M 1/3656* (2014.02); *A61M 1/106* (2013.01); *A61M 2205/13* (2013.01); *A61M 2205/3334* (2013.01)
USPC ......................................... 604/6.11; 210/646

(58) Field of Classification Search
USPC ............. 604/4.01, 6.11, 29–31, 90, 118, 119, 604/122, 149; 210/646, 739, 741
See application file for complete search history.

(56) References Cited

U.S. PATENT DOCUMENTS

| | | | |
|---|---|---|---|
| 3,882,861 | A | 5/1975 | Kettering et al. |
| 3,946,731 | A | 3/1976 | Lichtenstein |
| 4,450,527 | A | 5/1984 | Sramek |
| 4,501,583 | A | 2/1985 | Troutner |

(Continued)

FOREIGN PATENT DOCUMENTS

| | | |
|---|---|---|
| DE | 10245619 | 3/2004 |
| EP | 0330761 | 9/1989 |
| EP | 1399204 | 3/2004 |
| WO | 03/002174 | 9/2003 |

OTHER PUBLICATIONS

Chinese Office Action issued Apr. 3, 2013 for related Chinese Appln. No. 200980129174.5.

(Continued)

*Primary Examiner* — Philip R Wiest
(74) *Attorney, Agent, or Firm* — K&L Gates LLP

(57) ABSTRACT

A dialysis system includes: a blood filter; a dialysate pump connected to a dialysate portion of the blood filter; a blood pump connected to a blood portion of the blood filter, the blood pump including a diaphragm that is moved in cycles to pump the blood, the cycles having a flow period and a no-flow period; a patient access device in fluid communication with the blood portion of the blood filter, the no-flow period having a first characteristic of a property when the patient access device is lodged in a patient and a second characteristic of the property when the patient access device is dislodged from the patient; and a logic implementer configured to determine that the patient access device has been dislodged from the patient when the second characteristic of the parameter is detected.

20 Claims, 11 Drawing Sheets

(56) References Cited

U.S. PATENT DOCUMENTS

| | | |
|---|---|---|
| 4,534,756 A | 8/1985 | Nelson |
| 4,648,869 A | 3/1987 | Bobo, Jr. |
| 4,710,163 A | 12/1987 | Butterfield |
| 4,846,792 A | 7/1989 | Bobo, Jr. |
| 4,979,940 A | 12/1990 | Bobo, Jr. |
| 4,981,467 A | 1/1991 | Bobo, Jr. et al. |
| 5,026,348 A | 6/1991 | Venegas |
| 5,100,374 A | 3/1992 | Kageyama |
| 5,146,414 A | 9/1992 | McKown et al. |
| 5,350,357 A | 9/1994 | Kamen et al. |
| 5,427,695 A | 6/1995 | Brown |
| 5,454,374 A | 10/1995 | Omachi |
| 5,473,214 A | 12/1995 | Hildebrand |
| 5,557,263 A | 9/1996 | Fisher et al. |
| 5,723,775 A | 3/1998 | Watanabe et al. |
| 5,778,603 A | 7/1998 | Reppas |
| 5,790,036 A | 8/1998 | Fisher et al. |
| 5,863,421 A | 1/1999 | Peter, Jr. et al. |
| 6,071,421 A | 6/2000 | Brown |
| 6,077,443 A | 6/2000 | Goldau |
| 6,090,048 A | 7/2000 | Hertz et al. |
| 6,167,765 B1 | 1/2001 | Weitzel |
| 6,187,199 B1 | 2/2001 | Goldau |
| 6,221,040 B1 | 4/2001 | Kleinekofort |
| 6,572,576 B2 | 6/2003 | Brugger et al. |
| 6,575,927 B1 | 6/2003 | Weitzel et al. |
| 6,595,942 B2 | 7/2003 | Kleinekofort |
| 6,623,443 B1 | 9/2003 | Polaschegg |
| 6,736,789 B1 | 5/2004 | Spickermann |
| 6,767,333 B1 | 7/2004 | Müller et al. |
| 6,780,159 B2 | 8/2004 | Sandler et al. |
| 6,804,991 B2 | 10/2004 | Balschat et al. |
| 6,827,698 B1 | 12/2004 | Kleinekofort |
| 6,880,404 B2 | 4/2005 | Überreiter |
| 7,022,098 B2 | 4/2006 | Wariar et al. |
| 7,040,142 B2 | 5/2006 | Burbank |
| 7,052,480 B2 | 5/2006 | Han et al. |
| 7,172,569 B2 | 2/2007 | Kleinekofort |
| 7,172,570 B2 | 2/2007 | Cavalcanti et al. |
| 2001/0007930 A1 | 7/2001 | Kleinekofort |
| 2004/0171977 A1 | 9/2004 | Paolini et al. |
| 2004/0186409 A1* | 9/2004 | Cavalcanti et al. .......... 604/4.01 |
| 2005/0010118 A1 | 1/2005 | Toyoda et al. |
| 2005/0131331 A1 | 6/2005 | Kelly et al. |
| 2008/0065006 A1 | 3/2008 | Roger |
| 2008/0195021 A1 | 8/2008 | Roger |
| 2008/0195060 A1 | 8/2008 | Roger |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0088612 A1 | 4/2009 | Bouton |
| 2009/0088613 A1 | 4/2009 | Marttila |
| 2009/0088683 A1 | 4/2009 | Roger |
| 2009/0105627 A1 | 4/2009 | Rohde |
| 2010/0022935 A1 | 1/2010 | Muller |

OTHER PUBLICATIONS

European Search Report for International Application No. PCT/US2009/047589 mailed on Oct. 5, 2009.

Written Opinion of the International Searching Authority International Application No. PCT/US2009/047589 mailed on Oct. 5, 2009.

International Preliminary Report on Patentability for International Application No. PCT/US2009/047589 mailed on Oct. 28, 2010.

* cited by examiner

FIG. 5A

| Blood Flow Rate (mL/min) | $P_{va}$ Patient Pressure (mmHg) | $T_c$ Cycle Time (sec) | $P_d$ Outlet Drive Pressure (mmHg) | Lodged Venous Needle | | Dislodged Venous Needle | |
|---|---|---|---|---|---|---|---|
| | | | | $T_f$ Outlet Flow Period (sec) | $T_{nf}$ Outlet No Flow Period (sec) | $T_f$ Outlet Flow Period (sec) | $T_{nf}$ Outlet No Flow Period (sec) |
| 100 | 50 | 18 | 118 | 16.7 | 1.3 | 14.3 | 3.7 |
| | | | | 16.7 | 1.3 | 9.9 | 8.1 |
| | | | | 17.1 | 0.9 | 10.1 | 7.9 |
| | | | | 16.9 | 1.1 | 10.2 | 7.8 |
| | | | | 17.5 | 0.5 | 10.1 | 7.9 |
| | | | | 17 | 1 | 10.2 | 7.8 |
| 100 | 35 | 18 | 102 | 17.1 | 0.9 | 13.8 | 4.2 |
| | | | | 16.6 | 1.4 | 11.7 | 6.3 |
| | | | | 16.5 | 1.5 | 11.9 | 6.1 |
| | | | | 16.6 | 1.4 | 11.8 | 6.2 |
| | | | | 16.7 | 1.3 | 11.9 | 6.1 |
| | | | | 17.6 | 0.4 | 11.8 | 6.2 |
| 200 | 50 | 9 | 245 | 7.9 | 1.1 | 7.3 | 1.7 |
| | | | | 7.9 | 1.1 | 6.1 | 2.9 |
| | | | | 7.8 | 1.2 | 6 | 3 |
| | | | | 7.9 | 1.1 | 6 | 3 |
| | | | | 7.8 | 1.2 | 6.1 | 2.9 |
| 200 | 35 | 9 | 230 | 7.9 | 1.1 | 6.7 | 2.3 |
| | | | | 7.9 | 1.1 | 8.6 | 2.4 |
| | | | | 8 | 1 | 6.6 | 2.4 |
| | | | | 7.9 | 1.1 | 6.7 | 2.3 |
| | | | | 7.9 | 1.1 | 6.5 | 2.5 |
| | | | | 8 | 1 | 6.6 | 2.4 |
| 300 | 50 | 6 | 471 | 4.8 | 1.2 | 3.6 | 2.4 |
| | | | | 4.7 | 1.3 | 3.5 | 2.5 |
| | | | | 4.8 | 1.2 | 3.6 | 2.4 |

| Blood Flow Rate (mL/min) | $P_{va}$ Patient Pressure (mmHg) | $T_c$ Cycle Time (sec) | $P_d$ Outlet Drive Pressure (mmHg) | Lodged Venous Needle | | Dislodged Venous Needle | |
|---|---|---|---|---|---|---|---|
| | | | | $T_f$ Outlet Flow Period (sec) | $T_{nf}$ Outlet No Flow Period (sec) | $T_f$ Outlet Flow Period (sec) | $T_{nf}$ Outlet No Flow Period (sec) |
| 300 | 50 | 6 | 471 | 4.8 | 1.2 | 3.6 | 2.4 |
| | | | | 4.7 | 1.3 | 3.6 | 2.4 |
| 300 | 35 | 6 | 413 | 4.7 | 1.3 | 4.5 | 1.5 |
| | | | | 4.9 | 1.1 | 4.2 | 1.8 |
| | | | | 4.8 | 1.2 | 4.2 | 1.8 |
| | | | | 4.9 | 1.1 | 4.1 | 1.9 |
| 400 | 50 | 4.5 | 653 | 4.8 | 1.2 | 4.1 | 1.9 |
| | | | | 3.2 | 1.3 | 3 | 1.5 |
| | | | | 3.3 | 1.2 | 2.9 | 1.6 |
| | | | | 3.2 | 1.3 | 2.8 | 1.7 |
| | | | | 3.3 | 1.2 | 2.9 | 1.6 |
| 400 | 35 | 4.5 | 636 | 3.2 | 1.3 | 2.8 | 1.7 |
| | | | | 3.3 | 1.2 | 2.7 | 1.8 |
| | | | | 3.2 | 1.3 | 2.9 | 1.6 |
| | | | | 3.4 | 1.1 | 2.8 | 1.7 |
| | | | | 3.2 | 1.3 | 2.9 | 1.6 |
| | | | | 3.4 | 1.1 | 2.7 | 1.8 |
| | | | | 3.2 | 1.3 | 2.9 | 1.6 |
| | | | | 3.4 | 1.1 | 2.8 | 1.7 |

FIG. 5B

SYSTEM AND METHOD FOR DETECTING ACCESS DISCONNECTION

PRIORITY CLAIM

This application claims priority to and the benefit as a continuation application of U.S. Patent Application entitled, "System and Method for Detecting Access Disconnection", Ser. No. 12/180,331, filed Jul. 25, 2008, the entire contents of which are incorporated herein by reference and relied upon.

BACKGROUND

The present disclosure relates generally to patient access disconnection systems and methods for medical treatments. More specifically, the present disclosure relates to the detection of a patient access disconnection, such as the detection of needle or catheter dislodgment during dialysis therapy.

FIG. 1 illustrates a known access disconnection configuration. Blood is drawn from an arm 12 of a patient through an arterial line 14 connected the patient via an arterial needle 16. Blood is returned to the patient, after it has been treated, via a venous line 18 and venous needle 20. Needles 16 and 20 actually connect to a shunt 22, which is placed in fluid communication with one of the patient's arteries and veins. Accidental disconnection of the arterial line 14 during treatment is not as serious an issue as this simply eliminates the source of blood to the blood pump. Access disconnection of venous line 18 during treatment is a serious concern because arterial line 14 keeps feeding blood to the blood pump, while venous line 18 returns blood to a location outside of the patient.

A variety of different medical treatments relate to the delivery of fluid to, through and/or from a patient, such as the delivery of blood between a patient and an extracorporeal system connected to the patient via a needle or needles inserted within the patient. For example, hemodialysis, hemofiltration and hemodiafiltration are all treatments that remove waste, toxins and excess water from the patient's blood. During these treatments, the patient is connected to an extracorporeal circuit and machine, and the patient's blood is pumped through the circuit and machine. Waste, toxins and fluid are removed from the patient's blood, and the blood is infused back into the patient.

In these treatments, needles or similar access devices are inserted into the patient's vascular system so that the patient's blood can be transported to and from the extracorporeal machine. Traditional hemodialysis, hemofiltration and hemodiafiltration treatments can last several hours and are generally performed in a treatment center about three to four times per week. In in-center treatments, patients undergoing hemodialysis, for example, are monitored visually to detect needle dislodgment. However, the needle may not be in plain view of the patient or medical staff (e.g., it may be covered by a blanket) such that it could delay detection and timely response.

Moreover, in view of the increased quality of life, observed reductions in both morbidity and mortality and lower costs with respect to in-center treatments, a renewed interest has arisen for self-care and home therapies, such as home hemodialysis. Such home therapies (whether hemodialysis, hemofiltration or hemodiafiltration) can be performed during the day, evening or nocturnally. If unsupervised or asleep, dislodgment risks increase because a caregiver is not present and perhaps even the patient is not aware of a dislodgment.

Various systems exist for detecting needle dislodgement in hemodialysis. For example, U.S. Pat. No. 7,022,098 ("the '098 Patent") and U.S. Pat. No. 7,052,480 ("the '480 Patent"), both entitled Access Disconnection Systems And Methods, and assigned to the assignee of the present application, disclose access disconnection systems that measure an electrical impedance of the extracorporeal dialysis circuit connected to the vascular access needles. An external voltage or current source is used to inject a small current (e.g., less than 2.5 μ-Amp) into the blood flow. Here, sensitivity of the impedance system can be decreased when the patient is connected to earth ground (e.g., through grounding devices found in clinics and homes).

Another obstacle associated with systems that inject current into the extracorporeal circuit involves the addition of contacts to the disposable portion of the blood treatment system. Metal members placed in the disposable add to manufacturing difficulty and cost.

A need accordingly exists for an improved blood access disconnection system.

SUMMARY

The present disclosure sets forth systems and methods for determining when a needle or cannula has been removed from the patient. One primary use for the systems and methods is with blood treatments that remove blood from a patient and return, treat the blood in some manner, and return the blood to the patient. For example, hemodialysis ("HD"), hemofiltration ("HF"), hemodiafiltration ("HDF") and continuous renal replacement treatment ("CRRT") systems each remove blood from the patient, filter the blood, and return the blood to the patient. Besides these blood treatments, the access disconnection systems and methods discussed herein could be used in cardio pulmonary bypass surgeries in which blood is removed from the patient, oxygenated, and returned to the patient. Further, the access disconnection systems and methods could be used with single needle systems, such as certain medical delivery systems in which a drug or medicament is infused from a source to the patient. Additionally, the access disconnection systems and methods could be used in single or double needle aphaeresis or other blood separation and/or collection systems, such as for separating platelets, plasma, red cells or cell subpopulations.

The embodiments discussed herein have been tested using a diaphragm blood pump. It should be appreciated however that a diaphragm pump is not required for each of the present systems and methods. Each of the systems and methods, however, stops fluid flow periodically. With at least one type of pneumatically controlled diaphragm blood pump, the diaphragm is stopped at the end of a pump stroke in order to ensure that a full stroke has occurred and in one embodiment to calculate a volume of fluid that has just been drawn into the diaphragm pump chamber or pushed out of the chamber. The period of no-flow (or end-of-stroke ("EOS") time) is used to determine if an access disconnection has occurred. A peristaltic blood pump could be used alternatively. Here, the fluid flow is stopped or diverted every so often (e.g., once every five revolutions) to determine if an access disconnection has occurred.

In a first primary embodiment, the system measures a length of the no-flow period. The system monitors the cycle-to-cycle or stroke-to-stroke no-flow period to look for a lengthening of the period, which indicates an access disconnection. In a series of experiments, the system demonstrated that the length of the no-flow period increased when an access disconnection occurred and that the lengthening was significant enough to reliably predict an access disconnection.

The no-flow period can be detected in a number of different ways. In one embodiment, the system employs a fluid flow sensor that measures whether the blood is flowing or not. The flow sensor can be a non-invasive sensor. As discussed in more detail herein, if the no-flow period is short, e.g., a second, there will likely be a small flow of blood during the no-flow period due to system compliance (stretchiness of blood tubing). Thus while the flow sensor does not need to be highly accurate, it does need to be able to discern between higher flowrates and lower flowrates. The time during which low flowrate (or low flowrate dissipating to no-flowrate) is sensed is taken to be the no-flow time. It should be appreciated that the system does not have to actually wait until the no-flow period ends because the system knows the valve cycle time and thus knows the time of the end of the no-flow period. The system can therefore calculate the no-flow period as soon as flow stopping is sensed, increasing response time and sensitivity.

When the blood pump is a diaphragm pump driven by pneumatic or air pressure, the no-flow period can be determined alternatively from pressure readings taken of the drive pressure. For example, when positive pressure is applied to the diaphragm, the diaphragm moves to push fluid or blood out of the pump chamber. Eventually, the diaphragm deadends against the fluid side wall of the chamber, when all fluid has been pushed from the chamber. When this occurs, an air side pressure sensor senses a pressure spike, indicating a start of the no-flow period. Eventually, the system switches valves so that negative pressure is applied to suck the diaphragm away from the fluid wall and draw fluid or blood into the chamber.

The system does not need to wait for the negative pressure detection to mark the end of the no-flow period because the system sets and therefore knows when the valves are to switch to the negative drive pressure. That is, the system already knows the end of the no-flow period and can calculate the length of the no-flow period as soon as the positive pressure spike is sensed. The system can accordingly determine or suspect the needle status as soon as the positive pressure spike is sensed, which can prompt further testing, such as patient venous pressure testing. If needed however, the airside pressure sensor can be used to detect the negative pressure, marking the end of the no-flow period.

In a further alternative embodiment, a fluid pressure sensor placed on the downstream side of the blood pump is used to determine the no-flow period. Here, when the diaphragm closes against the fluid-side wall of the chamber, such that all blood has been forced out of the chamber, the downstream fluid or blood pressure sensor senses a drop in pressure, indicating the start of the no-flow period. Again, the system already knows when the pneumatic valves are to switch to apply negative pressure to the diaphragm for filling and does not have to wait for such event to mark the end of the no-flow period. Thus no-flow period and needle access status can be determined (or at least indicated) as soon as the downstream fluid pressure sensor senses the drop in fluid pressure.

If needed, an upstream fluid pressure sensor could be used to sense the negative blood fill pressure to signal the end of the no-flow period. The downstream fluid pressure sensor (and possible upstream sensor) can have a fluid-side component that is incorporated into a disposable cassette actuated by the dialysis instrument.

In a second primary embodiment, the system monitors the venous line pressure when the blood flow is stopped temporarily between diaphragm cycles (or when the peristaltic pump flow is stopped or diverted temporarily). In another series of experiments, the venous line pressure during the no-flow period of the pump cycle was shown to decrease when the venous needle was dislodged. Here too, the change in pressure was significant enough to reliably predict a needle dislodgement.

The sensor used for venous fluid pressure sensing can also have a fluid component that is cassette-based and located upstream of the venous access. It is expected that the fluid pressure will drop upon no-flow, and that it will drop to the patient's internal blood pressure. When the venous pressure instead drops below the patient's previously measured blood pressure, i.e., towards atmospheric pressure (plus residual pressure due to compliance), the system detects a dislodgement.

It is also contemplated to modify software to enhance the measurement taking during the no-flow periods. For example, the system can employ an algorithm that waits an additional period (lengthens the no-flow period) when it appears that an access disconnection has occurred to ensure that the measurement is not falsely triggering an alert event. Lengthening the no-flow period when a venous line pressure dip is detected increases measurement sensitivity (allows compliance to dissipate), which yields a more dramatic difference between access connected and access disconnected venous line pressures. Alternatively, the no-flow period is lengthened at all times, even during normal operation when access is connected, to a time sufficient to ensure that an accurate pressure reading has been taken.

It is further contemplated to combine the above two primary embodiments, such that both length of no-flow period and venous line pressure are monitored. The two detection methods can be performed simultaneously to provide a layer of redundancy. The system can for example be configured such that the detection of a lengthened no-flow period causes the blood pump no-flow time to be extended so that the venous line pressure can be measured for an extended period. Alternately, the lengthened no-flow detection in combination with a lower than expected "no-flow" venous line pressure triggers the extended venous line pressure monitoring period, so that the system can look for a lower than expected venous line pressure, confirming that an access disconnection has occurred.

It is accordingly an advantage of the present disclosure to provide an improved access disconnection system.

It is another advantage of the present disclosure to provide an access disconnection system that is non-invasive.

It is a further advantage of the present disclosure to provide an access disconnection system that does not require an electrical signal to be introduced into the blood circuit.

It is yet another advantage of the present disclosure to provide an access disconnection system that operates with an existing no-flow period of a diaphragm pump.

It is still a further advantage of the present disclosure to provide an access disconnection operable with system diaphragm and peristaltic pumps.

Moreover, it is an advantage of the present disclosure to provide an access disconnection system that is invisible to the patient, that is the system does not require the patient to take any steps for it to be enabled, and the patient cannot disable the system.

Additional features and advantages are described herein, and will be apparent from the following Detailed Description and the figures.

BRIEF DESCRIPTION OF THE FIGURES

FIGS. 5A and 5B are tables illustrating the effectiveness of measuring the no-flow period for detecting an access disconnection.

DETAILED DESCRIPTION

Figure 2:
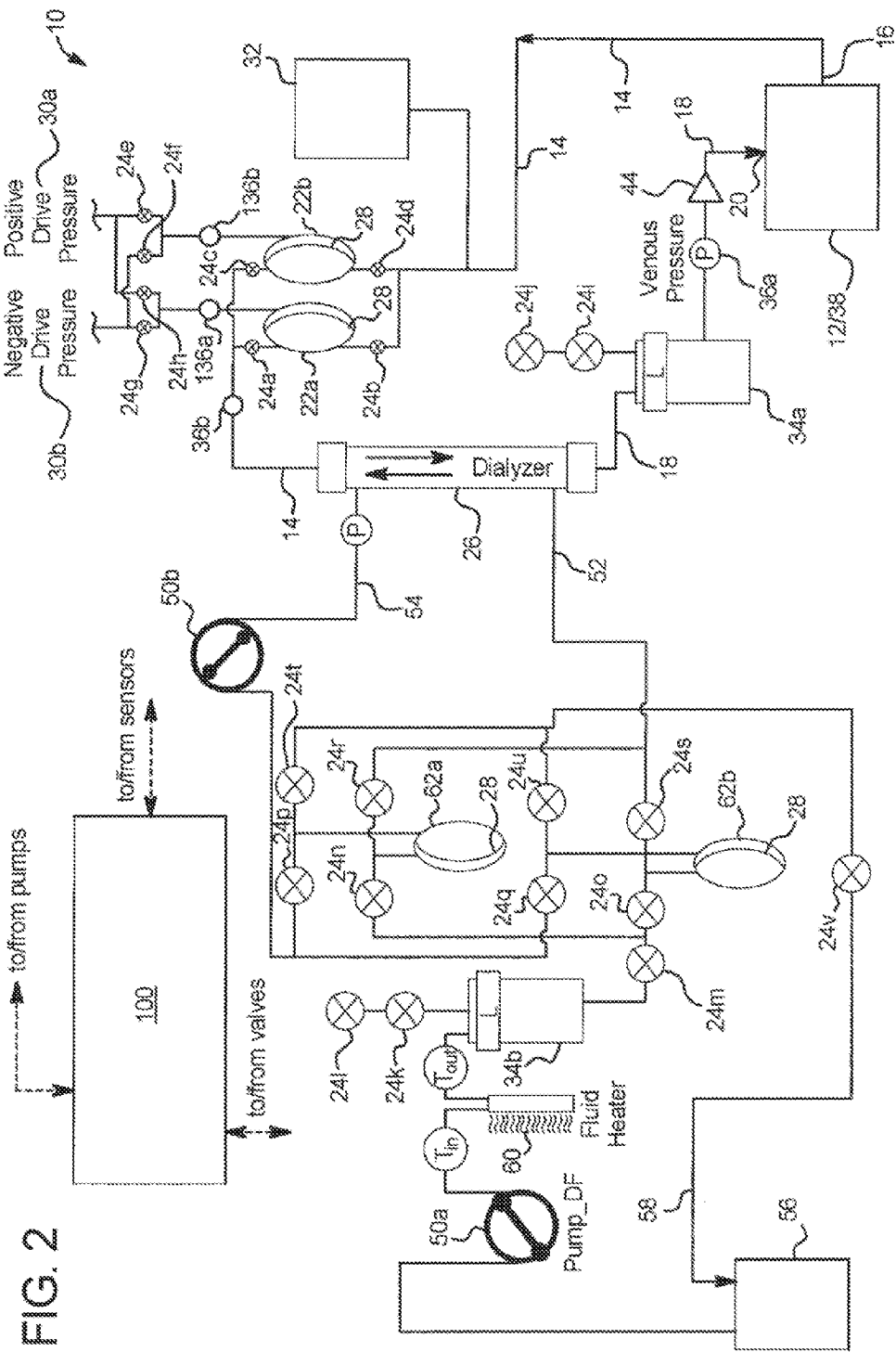
FIG. 2 is a schematic view of one embodiment of a dialysis system (both commercial and test set-up) operating with the access disconnection systems and methods of the present disclosure.

Referring now to the drawings and in particular to FIG. 2, system 10 illustrates one possible blood therapy treatment system for employing the access disconnection system ("ADS") and method of the present disclosure. System 10 connects to patient 12 via an arterial patient access device 16 and a venous patient access device 20. Patient access devices 16 and 20 are needles or cannulas, for example. Arterial patient access device 16 connects fluidly to arterial line 14. Venous patient access device 20 connects fluidly to venous or return line 18. The blood circuit formed via lines 14 and 18 can have additional components known to those of skill in the art, such as additional air traps, pressure sensors, blood leak detectors, line clamps and the like. The configuration of system 10 also shows components that were used in performing the tests rendering the results discussed below.

In the illustrated embodiment, a pair of diaphragm blood pumps 22a and 22b is connected to arterial line 14 via valves 24a to 24d as shown. Pumps 22a and 22b can be placed alternatively or additionally in fluid communication with venous line 18 via the valving arrangement shown in arterial line 14. In one embodiment, pumps 22a and 22b pump out of phase with each other, such that one of the pumps is pushing fluid to a blood filter or dialyzer 26, while the other pump is filling with blood from patient 12 via arterial access device 16 and arterial line 14. In the next cycle, the blood pumps switch operation, such that the second pump pumps to dialyzer 26, while the first pump fills with blood from patient 12. To fill with blood from patient 12, valve 24a or 24c is closed, while valve 24b or valve 24d is opened, respectively, for pumps 22a and 22b. When pumping to blood filter 26, the valve states switch, such that either valve 24b or valve 24d is closed, while valve 24a or valve 24c is opened, respectively, for pumps 22a and 22b. Detailed operation of a diaphragm 28 located within each of pumps 22a and 22b is discussed below.

System 10 in the illustrated embodiment uses a positive pressure source 30a and a negative pressure source 30b to drive diaphragms 28 within diaphragm pumps 22a and 22b. Valves 24e and 24h are opened to allow positive pressure to push diaphragm 28 of pump 22b or 22a, respectively, so as to push blood from the respective blood pump through valve 24c or 24a, respectively, to dialyzer 26. Valves 24f and 24g are opened to allow negative pressure from negative pressure source 30b to pull diaphragm 28 to one side of pump 22b or 22a, respectively, to pull blood from patient 12, through valve 24d or 24b to the respective blood pump.

Diaphragm pumps 22a and 22b in an alternative embodiment are replaced by a peristaltic pump, which is not operated pneumatically, such that positive or negative pressure sources are not needed. The no-flow periods are created by stopping the peristaltic pump rollers periodically, e.g., once every five revolutions, and taking a reading. It is believed that stopping the peristaltic pump periodically will operate well with at least the venous pressure measurement system and method for ADS discussed below beginning at FIG. 6.

System 10 in the illustrated embodiment performs hemodialysis (but could be modified to perform any of the treatments or therapies discussed in the Summary). Here, a fresh dialysate pump 50a pumps fresh dialysate via dialysate inlet line 52. A spent dialysate pump 50b pulls spent dialysate from dialyzer 26 via dialysate effluent return line 54. The dialysate portion of system 10 for performing hemodialysis is discussed in more detail below.

In an alternative embodiment, a substitution fluid, which can be dialysate that is further filtered so as to be injectable directly into the extracorporeal circuit, is fed directly via substitution fluid inlet line 52 instead, either downstream of a hemofilter 26 into venous line 18, or upstream of hemofilter 26 into arterial line 14 (for post- or pre-dilution hemofiltration, respectively). Further alternatively, substitution fluid line 52 is fed to both arterial line 14 and venous line 18 (to perform either or both pre- and post-dilution hemofiltration).

In a further alternative embodiment, system 10 performs hemodiafiltration. In such case, dialysis fluid inlet line 52 and dialysate effluent return line 54 are connected to blood filter 26 as is shown in FIG. 2. Additionally, a substitution fluid, such as ultrafiltered dialysate, is injected directly into the extracorporeal circuit, either at arterial line 14, venous line 18 or both arterial line 14 and venous line 18, as discussed above for the hemofiltration embodiment. In each of the hemodialysis, hemofiltration and hemodiafiltration embodiments, blood access is made via patient access devices 16 and 20. In each case, the access disconnection system discussed herein is capable of detecting if one of the access devices 16 or 20 is dislodged from patient 12.

Any of the hemodialysis, hemofiltration and hemodiafiltration embodiments can employ a saline bag 32 placed in fluid communication with arterial line 14 (or otherwise upstream of a blood pump) from which saline is pumped via pumps 22a and 22b through the arterial line 14 and venous line 18 for priming and rinseback for actual therapy. Saline from bag 32 was used to simulate blood in the experiments discussed. System 10 further includes an air trap 34a which removes air from blood returning via venous line 18 to patient 12. Vent valves 24i and 24j are sequenced to allow air to be vented to the atmosphere, without allowing ambient air to contact the patient's blood. A pressure sensor 36a is placed in venous line 18. Pressure sensor 36a measures the pressure of the blood returning to patient 12 and is used for the ADS and method of the present disclosure as discussed herein.

Figure 1:
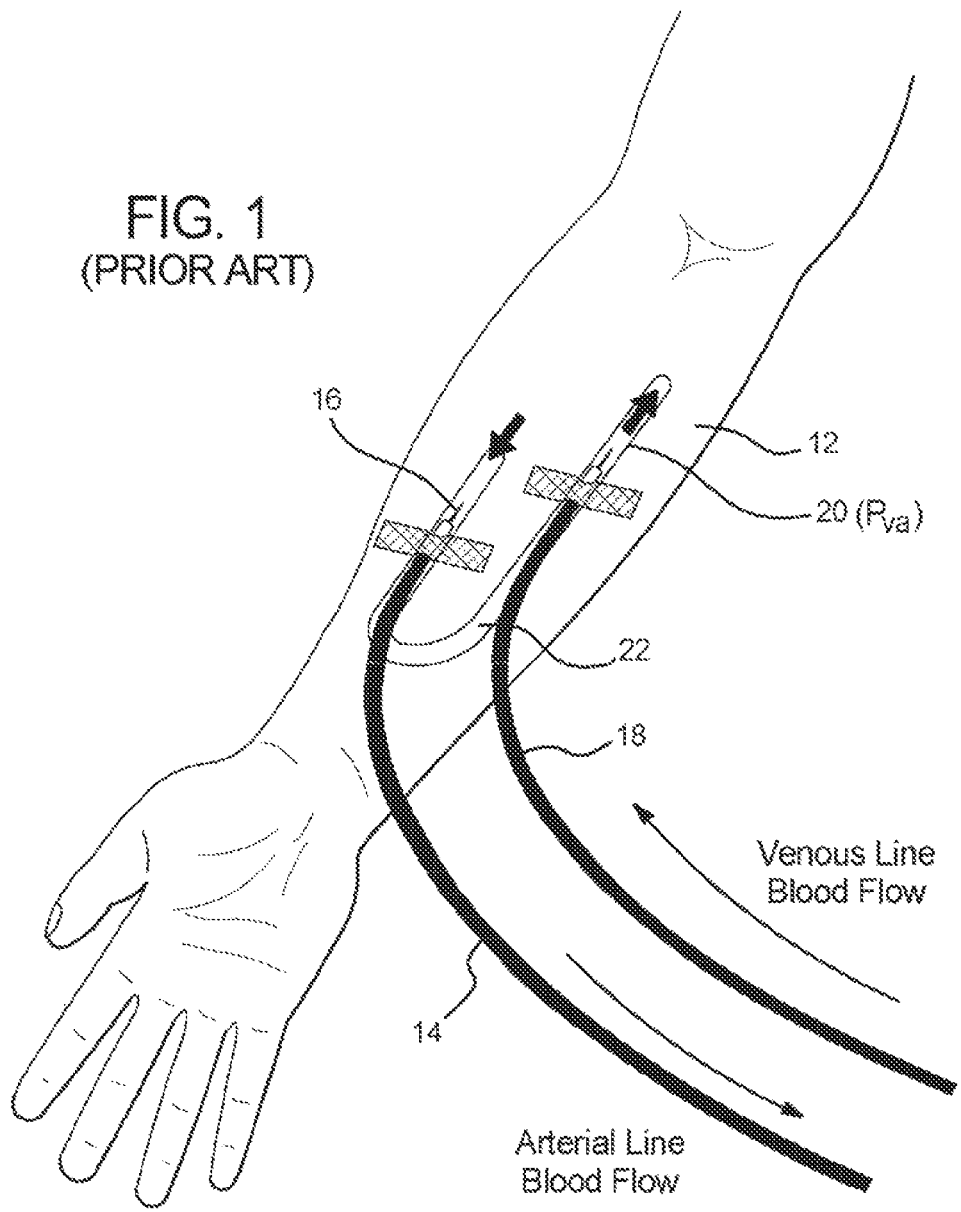
FIG. 1 is a schematic view of a patient blood access connection.

A pressure controlled chamber 38 is placed in the extracorporeal circuit for purposes of generating the test results shown below. Pressure control chamber 38 simulates the pressure that patient access device 20 sees at the patient. In various embodiments, pressure control chamber 38 simulates the patient's venous blood pressure to be approximately 35 to 50 mmHg Pressure control chamber 38 is shown to illustrate how the testing data below was generated. It should be appreciated however that in actual use, pressure chamber is not used. Pressure chamber 38 is in essence patient 12 in FIG. 1.

As discussed, the dialysate circuit includes a fresh dialysate pump 50a and a spent dialysate pump 50b, which circulate dialysate through dialyzer 26 via to-dialyzer line 52 and from-dialyzer line 54. The dialysate circuit also includes a dialysate supply 56, which can be one or more bagged dialysate supply or an online dialysate supply. For purposes of the experiment, supply 56 is modeled using a beaker of dialysate. Since the dialysate is not actually being used to clean the patient's blood, a drain line 58 is re-circulated back to beaker 56. In actual use, drain line 58 of system 10 is sent instead to a drain bag or a house drain.

Pump 50a pumps fresh dialysate through a heater 60 and a dialysate air trap 34b. Air trap 34b is in communication with vent valves 24k and 24l, which operate the same as vent valves 24i and 24j for air trap 34a. Valves 24m, 24n and 24l are sequenced to allow fresh dialysate to be pumped to a fresh side of each of balance chambers 62a and 62b. Balance chambers 62a and 62b are similar to diaphragm pumps 22a and 22b in that they each have a diaphragm 28 that moves back and forth within a fixed volume chamber. The primary difference between balance chambers 62a and 62b and diaphragm pumps 22a and 22b is that fluid is pumped to both sides of diaphragm 28 within the balance chambers. On the other hand, as discussed, blood pumps 22a and 22b are operated in one embodiment by pumping air to the non-fluid side of diaphragm 28.

Valves 24p and 24q selectively allow spent dialysate pump 50b to pump spent dialysate to the spent dialysate side of diaphragms 28 of balance chambers 62a and 62b, respectively. Pumping spent dialysate into either of balance chambers 62a and 62b causes diaphragm 28 to push fresh dialysate from the fresh side of the respective balance chamber through fresh outlet valve 24r or 24s, respectively, to dialysate input line 52 and dialyzer 26. When fresh dialysate is pumped into the fresh side of balance chambers 62a and 62b, diaphragm 28 is moved to push spent dialysate from the balance chambers, through spent outlet valves 24t and 24u, through drain line 58 and drain valve 24v to drain (or for experimental purposes back to the supply or beaker 56 as shown).

Balance chambers 62a and 62b and associated valves 24m through 24v ensure that a same amount of fresh fluid delivered to dialyzer 26 is removed as spent or effluent dialysis fluid from the dialyzer. To control ultrafiltration, a known amount of additional spent fluid is removed from dialyzer 26. The only source of additional fluid is the patient's excess blood water gained over the time from the last blood treatment therapy. One system and method for using a pair of balance chambers 62a and 62b to additionally control the volume of ultrafiltration removed from the patient is discussed in co-pending patent application, assigned to the assignee of the present disclosure entitled "High Convection Home Hemodialysis/Hemofiltration and Sorbent System, U.S. Ser. No. 10/982,170, filed Nov. 4, 2004e relevant portions of which are incorporated herein expressly by reference.

A logic implementer 100 is programmed to operate system 10. Logic implementer 100 can include one or more processor and one or more memory, such as a random access memory ("RAM") and a read only read only memory ("ROM"). The processors can be structured to have a supervisory processor that runs a plurality of delegate processors. The delegate processors are split to run different groups of related functions. For example, one delegate processor can be dedicated to receiving sensor inputs from the pressure sensors (e.g., venous line pressure sensor 36a), temperature sensors, blood leak detectors and the like, while another processor controls valves 24 (referring collectively to valves 24a to 24v), while still another delegate processor controls heater 60.

The master processor, the delegate processor dedicated to sensing, or some other processor of logic implementer 100 runs an algorithm according to the procedures set for below that take system readings, analyze the readings, and determine if an access disconnection has occurred. In one embodiment, if an access disconnection is determined, logic implementer 100 clamps one or both arterial line 14 and venous line 18, stops blood pumps 22a and 22b and halts dialysate pumps 50a and 50b. Logic implementer 100 also provides an audio, visual or audiovisual alarm warning the patient or caregiver of the access disconnection.

Much of the apparatus shown in FIG. 2 can be incorporated into or associated with a disposable cassette. Valves 24 can for example be volcano valves placed in the disposable cassette as described in U.S. Pat. No. 5,350,357 ("the '357 Patent") entitled, "Peritoneal Dialysis Systems Employing A Liquid Distribution And Pumping Cassette That Emulates Gravity Flow", the entire contents of which are incorporated herein be reference." The '357 Patent also shows placement of a diaphragm pump chamber in a disposable cassette. With a cassette-based system, much of the fluid lines of system 10 are provided as rigid pathways in the cassette. Flexible tube run from the cassette to external entities, such as patient 12, supply 56 and a drain. Filter 26 can be an external device to the cassette or provided with the cassette. Alternatively the components in FIG. 2 are connected primarily via tubing, which is opened and closed via pinch valves.

Figure 3:
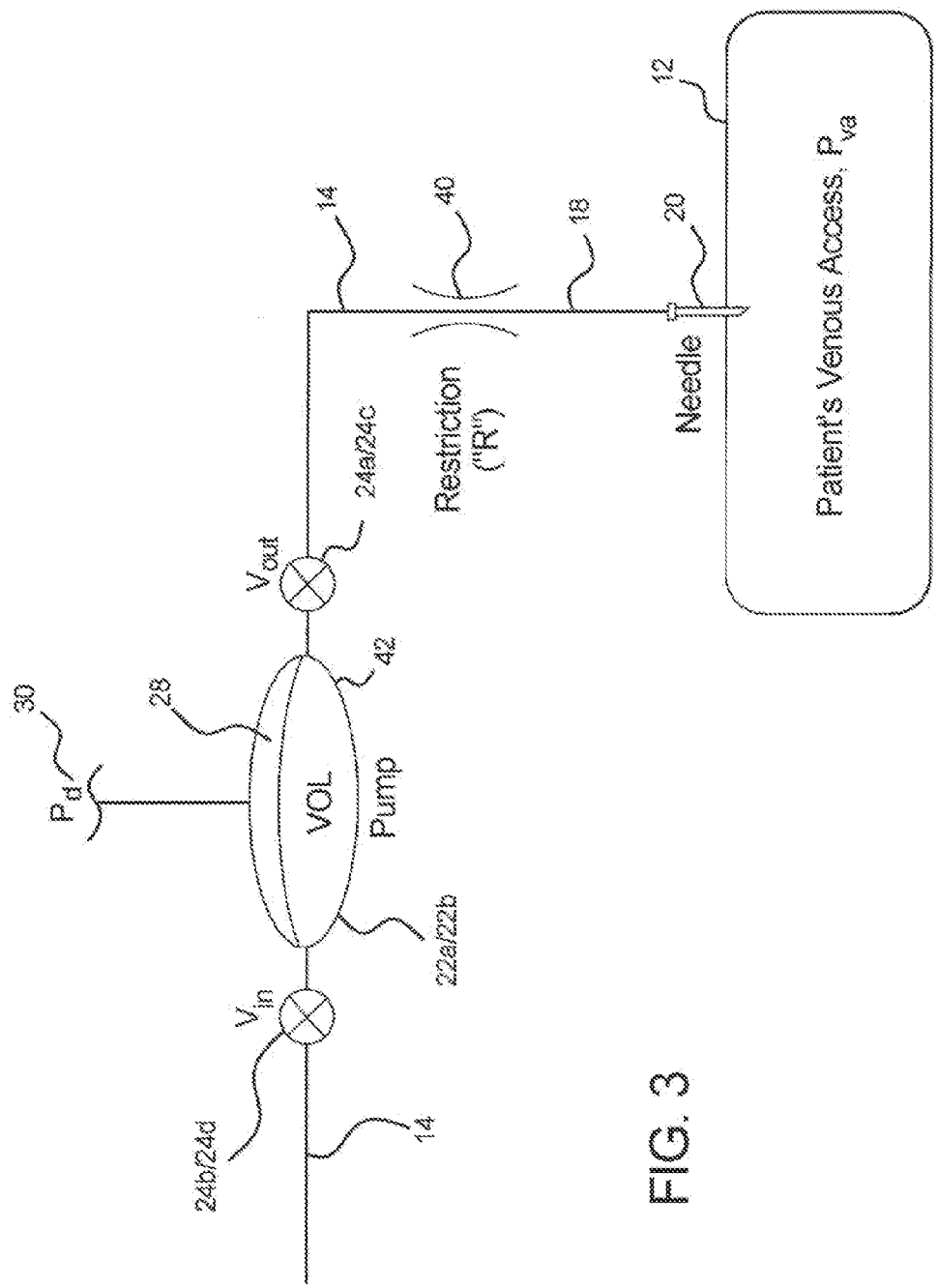
FIG. 3 is a simplified schematic view of one embodiment of a venous line portion of the blood circuit illustrating the access disconnection systems and methods of the present disclosure.

Referring now to FIG. 3, a simplified drawing showing a blood pump 22 (referring to either blood pump 22a or 22b of FIG. 2) and associated inlet valve $V_{in}$, and outlet valve $V_{out}$ (referring to either of inlet valves 24b or 24d and outlet valves 24a or 24c) is illustrated. Pump 22 as discussed above has a diaphragm 28, which is controlled via pneumatic pressure $P_d$ applied by positive and negative pressure drives 30 (referring collectively to both pressure drives 30a and 30b discussed in FIG. 2). In FIG. 3, components upstream of blood pump 22 are not shown for ease of illustration. Also, components between blood pump 22 and venous needle 20, such as dialyzer 26, venous air trap 34a and a particulate filter (not shown in FIG. 2) are combined into a single component illustrated as restriction 40. Restriction 40 is taken to have a combined flow resistance R. Diaphragm pump drive pressure is shown as $P_d$, as mentioned, while the venous blood pressure of patient 12 is labeled $P_{va}$.

In one embodiment, system 10 adjusts drive pressure $P_d$ to pump blood via diaphragm pump 22, such that the pump achieves consistent periods of blood flow and resulting near constant periods of no-flow just prior to the diaphragm valves $V_{in}$ and $V_{out}$ being act upon or switched. The period between the switching of valves $V_{in}$ and $V_{out}$ (cycle period) and the volume VOL defined within fluid chamber wall 42 of blood pump 22 (the pump stroke volume) control the average blood flowrate. Thus, blood flowrate can be modeled as follows:

blood flowrate=pump stroke volume VOL/cycle period $T_c$

To ensure that full strokes of diaphragm pump 22 are delivered with each pump cycle (full volume VOL), system 10 in one embodiment adjusts the drive pressure $P_d$ of pneumatic source 30 so that some period of no blood flow occurs with each cycle. The period of no blood flow is typically small and can be controlled by system 10 to be a constant for a given blood flowrate. Also, the '357, describes a system for calculating an amount of fluid pumped by the diaphragm pumps, which uses no-flow or end-of-stroke period to perform calculations associated with fluid measuring system.

When the blood pump is a peristaltic pump, the volumetric control of the blood pumping can be determined using a single balance chamber, like chambers 62a and 62b in which the peristaltic pump pumps flood from the same line to both sides of the balance chamber.

Using No-Flow Period to Detect Access Disconnection

Figure 4:
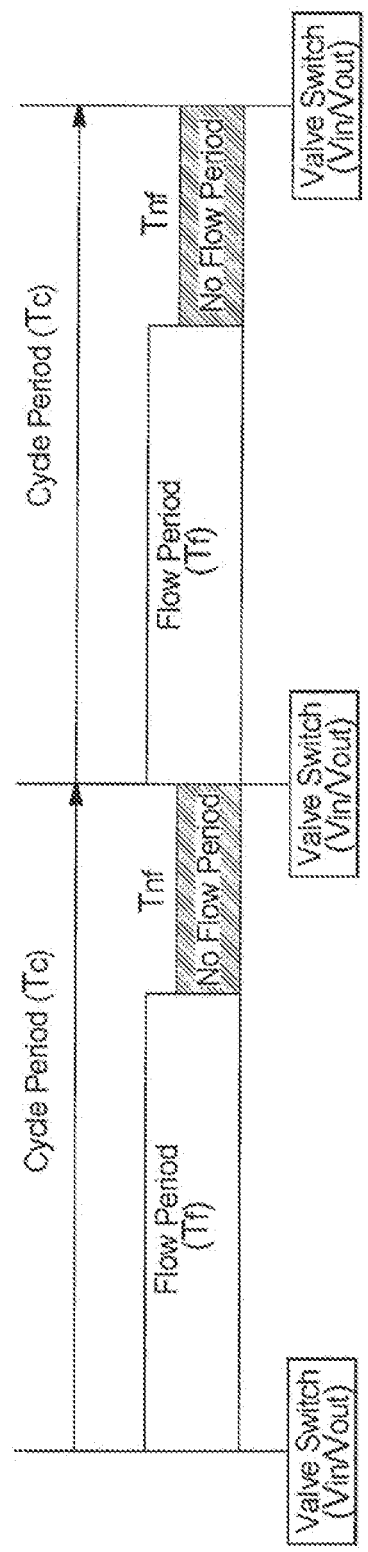
FIG. 4 is a schematic timeline illustrating the flow and no-flow periods associated with the operation of one diaphragm pump.

Referring now to FIG. 4, two blood pump cycle periods are shown schematically. Inlet valve $V_{in}$ and outlet valve $V_{out}$ are switched at different points in time as shown in FIG. 4, causing the two illustrated cycle periods. The cycle period time is shown as time $T_c$. The portion of total cycle time $T_c$ for blood flow is shown as $T_f$. The remaining portion of total cycle time $T_c$ for the no-flow period is shown as $T_{nf}$.

The difference between drive pressure $P_d$ and the venous access pressure $P_{va}$ controls a flow period $T_{nf}$. The flow period $T_f$ is the difference between desired cycle time $T_c$ and no-flow period $T_{nf}$. The drive pressure $P_d$ required to achieve a given no-flow period $T_{nf}$ is dependent upon several factors, such as stroke volume VOL, desired cycle time $T_c$, desired no-flow time $T_{nf}$, flow restriction R, and the patient's venous access pressure $P_{va}$. Since the volume VOL of pump 22 is constant and flow restriction R for a given flowrate is constant, and since at steady state drive pressure $P_d$ and desired cycle time $T_c$ are constant, a measured change in no-flow period must result from a change in patient's venous access pressure $P_{va}$. And, even though the drive pressure $P_d$ is manipulated to a setting that attempts to achieve a desired no-flow period $T_{nf}$, the no-flow period will vary even when drive pressure $P_d$ applied is accurate, if the patient's venous access pressure $P_{va}$ has changed. And since the patient's venous access pressure $P_{va}$ changes fairly significantly upon a needle dislodgement (e.g., 50 mmHG to zero mmHG), the corresponding no-flow period should be readily detectable. There is accordingly a no-flow period (for a given set of parameters) that is characteristic of the venous needle being lodged in the patient and a no-flow period that is characteristic of the venous needle being dislodged from the patient.

Given a constant drive pressure $P_d$ and cycle time $T_c$ (set by the desired blood flowrate), a change in measured venous access pressure $P_{va}$ (e.g., due to an access disconnection) causes a change of the no-flow period $T_{nf}$. In particular, a decrease in venous access pressure $P_{va}$ (e.g., due to a needle dislodgement) results in an increase in no-flow period $T_{nf}$ due to an increase in pressure change. The reason for this relationship is based on fluid dynamics where $\Delta P = \lambda*L/D*\rho/2*\omega^2$, where $\lambda$=friction constant, L=length of fluid pathway, D=average diameter of fluid pathway, $\rho$=density of fluid, $\omega$=fluid velocity, which can be generalized as: $\Delta P = K*Flow^2$, or $\Delta P = K*(\Delta V/\Delta T)^2$, wherein $\Delta P = P_d - P_{va}$;

$\lambda$, L, D, $\rho$ and K are at least substantially constant. $\Delta V$ is a change in fluid volume by the movement of diaphragm 28 within the fixed volume pump chamber 22, thus $\Delta V$ is constant. $\Delta T$ is the time of fluid flow or $T_f = T_c - T_{nf}$. Cycle time $T_c$ is set. Since $\Delta V$ and $T_c$ are constants, $T_{nf}$, has to change and has to decrease in response to the $\Delta P$ increase. In essence, the internal volume of the chamber, the switching of the valves or cycle time and drive pressure are either inherently constant or held constant. An access disconnection that results in an upstream pressure change from the patient's internal blood pressure to atmospheric pressure results in less resistance to drive pressure $P_d$, which results in the diaphragm 28 moving faster for the given drive pressure, reaching an end of stroke sooner, and in turn allowing for more time (no-flow) until the valves switch again for the next stroke.

The instantaneous increase in no-flow period $T_{nf}$ is detected by a sensor and one or more processor controlling system 10. Logic implementer 100 is in turn programmed or configured to determine that an access disconnection of return needle 20 has occurred and take appropriate action described above, such as a visual or audio-visual alarm, the stopping of blood pumps 22a and 22b, the closing blood line clamps or valves (such as valves 24a to 24d) and the stopping dialysate pumps 50a and 50b shown in FIG. 2.

In one embodiment, as seen in FIGS. 6 to 10, a pressure signal can be used to determine the length no-flow period $T_{nf}$. For example, pneumatic drive pressure $P_d$ can be monitored to detect a pneumatic pressure spike indicating an end of stroke of the diaphragm 28 within one of the chambers of the blood pumps 22. The pressure spike starts the period of no-flow $T_{nf}$. The ensuing sensed pneumatic drive pressure change to a negative drive pressure $P_d$ to move diaphragm 28 in the opposite direction ends the no-flow period $T_{nf}$. Pneumatic pressure sensors 136a and 136b (which are mounted within the dialysis machine) illustrate one possible place to position the air pressure sensors to make such measurements. Both measure positive and negative pneumatic drive pressures from sources 30a and 30, respectively. When positive drive pressure $P_d$ pushes diaphragm 28 against the fluid side wall of chamber 42, such that all blood or fluid is expelled from the pump chamber, the corresponding pressure sensor 136a (or 136b) detects a spike in air pressure, which marks the beginning of the no-flow period $T_{nf}$ for the particular blood pump chamber.

The end of the no-flow period does not have to be measured because it is already known. As discussed, cycle time $T_c$ is set and known, so that system 10 knows when valves 24e to 24h are to switch to apply negative pressure to a respective diaphragm 28 and does not have to wait for such even to occur to actually determine the no-flow time. For example, one cycle time tested below in the experiments is nine seconds. If a positive pressure spike is seen at pressure sensor 136a or 136b, for example, 5.5 seconds after a pump-out stroke for one of pumps 22a and 22b has begun, system 10 knows at that instant that the no-flow period is going to be 4.5 seconds (9 seconds–5.5 seconds) and does not have to wait the additional 4.5 seconds to make a determination of whether needle 20 is lodged or not.

Thus, a significant amount of time is saved and the system can react quicker. System 10 can also act more thoroughly. For example, if the positive pressure spike at pressure sensor 136a or 136b occurs too soon after pump-out stroke begins, indicating that there might be a needle dislodgment, system 10 can immediately focus, during the actual no-flow period, on venous fluid pressure sensor 36a to look for a corresponding drop in pressure from the patient's expected internal blood pressure (to or close to atmospheric pressure), further indicating a needle dislodgment. One possible decision tree programmed into logic implementer 100 of system 10 stops the blood and dialysate pumps, closes appropriate valves/clamps and alerts the patient if both air pressure sensor 136a or 136b and venous fluid pressure sensor 36a indicate a needle dislodgment. If only air pressure sensor 136a or 136b via the no-flow determination indicates a needle dislodgment, system 10 allows the other blood pump 22a or 22b to pump out its volume of blood and uses both pressure sensors to look again for an indication of dislodgment. If any indication occurs, system 10 takes action as described. If not, system 10 allows therapy to continue.

It should be appreciated however that, if needed, pressure sensor 136a (or 136b) could be used to detect a negative air pressure applied to pull diaphragm 28 from the fluid-side wall of chamber 42, filling the chamber with blood, to signal and end of the no-flow period to logic implementer 100. This could be done for both pump chambers 22a and 22b.

In an alternative embodiment, a fluid pressure sensor is used to determine the no-flow period. In the illustrated example, fluid pressure sensor 36b resides downstream of pump chambers 22a and 22b. When a diaphragm 28 closes against the fluid-side wall of respective chamber 42, such that all blood has been pumped from the chamber, downstream blood pressure sensor 36b senses a pressure drop, which starts the no-flow period. In one embodiment, the fluid-side or component of fluid pressure sensor 36b is located within a disposable cassette.

Here too, the end of the no-flow period does not have to be measured because it is already known, such that system 10 can react quickly as soon as the pump-out end-of-stroke fluid pressure drop is sensed. For example, if the fluid pressure drop sensed at fluid pressure sensor 36b (indicating end-of-pump-out-stroke) occurs too soon after the pump-out stroke begins, indicating that there might be a needle dislodgment, system 10 can then immediately focus, during the actual no-flow period, on venous fluid pressure sensor 36a to look for a corresponding drop in pressure from the patient's expected internal blood pressure (to or close to atmospheric pressure), further indicating a needle dislodgment. The above-described decision tree is also applicable here.

Although not illustrated, if needed, an additional fluid pressure sensor could be placed upstream of pump chambers 22a and 22b, which would sense a negative fluid pressure pulling fluid into one of the pump chambers, signaling an end the no-flow period to the logic implementer 100. This pressure sensor could also have a fluid-side component that is placed in a disposable cassette.

In a further alternative embodiment, a flow sensor 44 is positioned to detect blood flow in venous line 18. A signal from the sensor is used to determine the length of no-flow period. Examples of suitable flow sensors include a non-invasive flow sensor provided by Transonic Systems Inc.®, Ithaca, N.Y., Models HD02 or HD03. Fluid flow sensor 44 does not need to be highly accurate but should respond quickly to rapid drops in fluid flow and rapid rises in fluid flow. When the diaphragm 28 dead-ends against the fluid-side walls of chambers 42, blood flow will drop quickly even if it does not drop all the way to zero flow. Regardless, the leading edge of the drop marks the beginning of the no-flow period. Likewise, the leading edge of a flow increase sensed by sensor 44 marks the end of the no-flow period. Fluid flow sensor 44 in one embodiment is located on the dialysis machine and interfaces with the venous line 18, e.g., directly after it exits dialyzer 26 or a disposable pumping and/or valving cassette.

Regarding the operation of flow sensor 44, the end of the no-flow period of a first blood pump 22a or 22b indicated by the sensing of blood flow from second pump 22b or 22a still coincides with when air valves 24e to 24h are switched. The total cycle time $T_c$ sensed by flow sensor 44 (leading edge of flow initially detected (due to one of blood pumps 22a and 22b) to leading edge of flow initially detected (due to the other of blood pumps 22a and 22b) tracks or equals the time set between the switching of valve states. And the period of flow $T_f$ sensed by flow sensor 44 (e.g., leading edge of flow detected to falling of flow detected) equals the time of flow sensed by the air or fluid pressure sensors (e.g., time from when air valves 24e/24f or 24g/24h are switched for positive pressure to when positive pressure spike is sensed). Since cycle time $T_c$ is known from the valve states, and flow period $T_f$ is sensed via flow sensor 44, no-flow period $T_{nf}$ can be calculated from the two at the instant the flow period $T_f$ ends. System 10 again does not have to wait for a sensed end to the no-flow period $T_{nf}$ to evaluate whether the no-flow period $T_{nf}$ is longer than expected (or flow period $T_f$ shorter than expected), indicating or suggesting that an access disconnection has occurred. Again, a significant amount of time is saved, and the system can react quicker and more thoroughly.

For example, if the end of flow sensed by flow sensor 44 occurs too soon after the leading edge of flow is sensed by flow sensor 44, indicating that there might be a needle dislodgment, system 10 can then immediately focus, during the actual no-flow period, on venous fluid pressure sensor 36a to look for a corresponding drop in pressure from the patient's expected internal blood pressure to or close to atmospheric pressure, further indicating a needle dislodgment. The above-described decision tree is also applicable here.

The ADS system of the present disclosure accordingly looks for a first characteristic no-flow time period $T_{nf}$ to determine that venous access device 20 is properly lodged in the patient. The ADS system and method looks for a second characteristic no-flow period $T_{nf}$ which is longer than the first characteristic no-flow period $T_{nf}$ to determine that the venous access needle 20 is dislodged from patient 12. And because system 10 already knows the end of no-flow period $T_{nf}$, system 10 can look for the beginning of the no-flow period to obtain an indication of whether a needle dislodgment has occurred. Another way of stating this is that system 10 looks for a flow period $T_f$ that is shorter than expected to determine (or suspect) that the venous access needle 20 is dislodged from patient 12.

An experiment using system 10 shown in FIG. 2 was performed to test the ability of sensing no-flow period $T_{nf}$ to determine if an access disconnection has occurred. The data was taken using worst case-type conditions, including a seventeen gauge venous needle for venous access device 20 (typically smallest diameter needle, providing the highest pressure drop, used to provide patient access for hemodialysis, hemofiltration, etc.) and patient access pressures $P_{va}$ below 50 mmHg Dialysate side flowrate was set at approximately 200 ml per minute. Other control parameters for during the experiment included drive pressure $P_d$, total flow period $T_f$ and no-flow period $T_{nf}$. 0.9% saline was used in the experiment instead of blood.

FIGS. 5A and 5B show the results of the experiment over blood flowrates ranging from 100 to 400 mL/min, which encompasses typical blood flowrates for hemodialysis and hemofiltration therapies. Cycle time $T_c$ was varied between 4.5 and 18 seconds, which corresponds to blood flowrates of 400 to 100 mL/min, by cycling valves 24a to 24d at different rates. That is, blood flowrates were varied by varying cycle time $T_c$. Drive pressure $P_a$ was varied between a lower end of about 100 mmHg to about 650 mmHg Patient access pressure $P_{va}$ was varied between about 35 and 50 mmHg using tank 38.

The results in each scenario show a significant lengthening of no-flow period or time $T_{nf}$ when venous access device 20 is dislodged. Logic implementer 100 is accordingly programmed or configured for a given set of input parameters including blood flowrate, total cycle time $T_c$ and drive pressure $P_d$ to look for a lower range of no-flow times to determine that venous access device 20 is lodged and that treatment can continue. Logic implementer 100 is programmed or configured to look either (i) for a particular increase or delta in no-flow time $T_{nf}$ to accelerate to an unacceptable level or (ii) for no-flow time $T_{nf}$ to rise above a threshold level, at which time an access disconnection condition is determined and appropriate action taken.

As seen, the increase is most pronounced at lower blood flowrates and higher patient access pressures $P_{va}$, but even at the highest blood flowrate of 400 mL/min and lowest patient pressure of 35 mmHg, no-flow period $T_{nf}$ was measured to increase on an average by more than 30%. Thus, by controlling or knowing a set of input parameters including total cycle time $T_c$, access type/needle gauge and drive pressure $P_d$, the system can measure indirectly the patient's venous access pressure $P_{va}$, which is in an inversely proportional relationship (as seen below) to the square of a measurable flow period of the diaphragm pump. Another way of describing the change in pressure versus the no-flow period $T_{nf}$ as follows:
$\Delta P=K(\Delta V/\Delta T)^2 =>P_d-P_{va}=K*\Delta V^2/(T_c-T_{nf})^2 =>P_{va}=P_d-K*\Delta V^2/(T_c-T_{nf})^2 =>P_{va}=K_{pd}-K_{v2}/(T_c-T_{nf})^2 =>P_{va}=K_{pd}-K_{v2}/(T_c^2-2T_cT_{nf}+T_{nf}^2) =>P_{va}=K_{pd}-K_{v2}/(K_{tc2}-K_{tc}T_{nf}+T_{nf}^2)$.
In this last equation, the patient's venous access pressure $P_{va}$ is described as a series of constants for drive pressure, cycle time and chamber volume, which are constant at least for a given flow rate condition. The final equation shows that $P_{va}$ is proportional to a relationship that includes several constants, and the inverse of $T_{nf}$ plus the square of $T_{nf}$.

Using Venous Pressure Measurement to Detect Access Disconnection

System 10 in an alternative method of detecting venous needle dislodgment in an extracorporeal circuit (using a diaphragm pump having end of stroke no-flow periods or a peristaltic pump that is stopped incrementally to have no-flow periods) attempts to measure the patient's venous access pressure $P_{va}$ (actual pressure in patient's vascular access) using the venous line pressure sensor 36a (which can also have a fluid side or component that is cassette-based) upstream of the needle 20, as opposed to measuring the no-flow period as discussed in the first primary embodiment. When flow is stopped the pressure in the venous line should drop but not below the patient's actual blood pressure $P_{va}$ if the needle is inserted into the patient's vascular access. If the needle is removed, the pressure "downstream" of the needle changes from the patient's blood pressure or $P_{va}$ to atmospheric pressure. This second embodiment looks for a pressure drop at venous line pressure sensor 36a that would indicate that the pressure "downstream" of the needle is atmospheric and that the needle has been dislodged.

In an extracorporeal circuit that uses a constantly moving peristaltic pump, the venous pressure measurement can be less effective in detecting venous needle dislodgement since the pressure drop across the venous needle (due to the constant blood flow) is much larger than the pressure downstream of the venous needle (pressure in patient's vascular access). Therefore when the venous needle becomes dislodged, the pressure drop across the needle can be expected to be reduced by the patient's own venous pressure, e.g., by about 50 mmHg or less. When compared to a venous line pressure that is averaging over 200 mmHg (and fluctuating), the change in mean pressure can be masked, hence the need to measure during the no-flow period.

When the diaphragm pump is used to deliver the blood in the extracorporeal circuit, the flow through the venous needle drops to zero (or close to it) between chamber cycles or during the no-flow period $T_{nf}$. During this period, venous line pressure transducer or sensor 36a monitor measures the pressure downstream of the venous needle $P_{va}$ without the influence of the pressure drop across the needle due to the blood flowrate. In this way, by monitoring the venous pressure between diaphragm pump cycles, venous needle dislodgment can be detected through a drop in venous access pressure $P_{va}$ sensed by sensor 36a.

Figure 6:
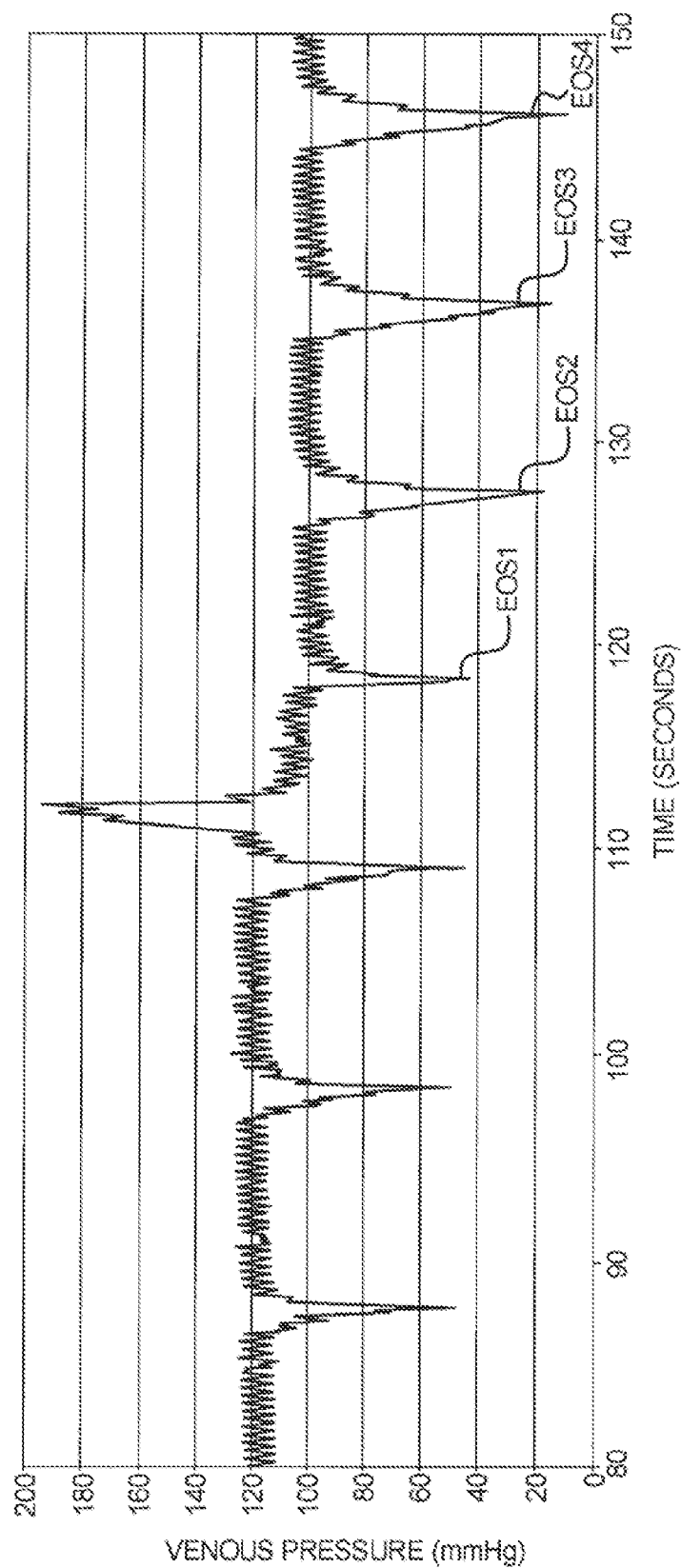
FIG. 6 is a graph illustrating the effect an access disconnection has on venous line pressure for one blood flowrate, patient venous access pressure (actual pressure in the patient's vascular access) and end-of-stroke time setting.

FIG. 6 shows the results of an experiment performed using the fluid path circuit of system 10 that was used in the no-flow sensing experiment. During the experiment of FIG. 6, much the same procedure was used. Venous access pressure $P_{va}$ was still controlled in chamber 38, simulating a patient's access, and the venous pressure in line 18 was measured by the venous pressure transducer 36a. During the experiment of FIG. 6, a patient pressure $P_{va}$ of 35 mmHg was used as a worst case value, a patient's access pressure should be greater than 50 mmHg Further, blood flowrate was set to be 200 mL/min, and end-of-stroke ("EOS") or no-flow period $T_{nf}$ was set to be one second.

The data in the FIG. 6 chart shows a venous needle 20 dislodgement occurring between time 110 and 120 as a spike in pressure. This spike was product of the way the dislodgement event was simulated. The patient's blood access was simulated by a blood tubing injection port. As the needle was pulled out of the blood access port, the end of the needle was temporarily sealed against the injection port body causing the spike in pressure. Such pressure spike may or may not occur with an actual patient 12, however, if such a spike does prove to be common, it is contemplated to program or configure logic implementer 100 of system 10 to look for a venous pressure spike occurring immediately prior to a venous pressure drop as further evidence that an access disconnection has taken place.

In FIG. 6, the graph shows EOS (no-flow periods $T_{nf}$) events occur approximately every nine to ten seconds, which would be typical for a 200 mL/min blood flowrate. Prior to the dislodgement event, the venous pressure measured via sensor 36a during the no-flow periods $T_{nf}$ or EOS events ranged between 45 and 50 mmHg. After the dislodgement event, the venous pressure measured at pressure sensor 36a and during the no-flow periods $T_{nf}$ (EOS events 1 to 4 in FIG. 6) dropped to less than 20 mmHg. It is believed that the difference is not evident on the first no-flow period $T_{nf}$ (EOS 1) after dislodgement due to effects associated with the dislodgement simulation discussed above.

Figure 7:
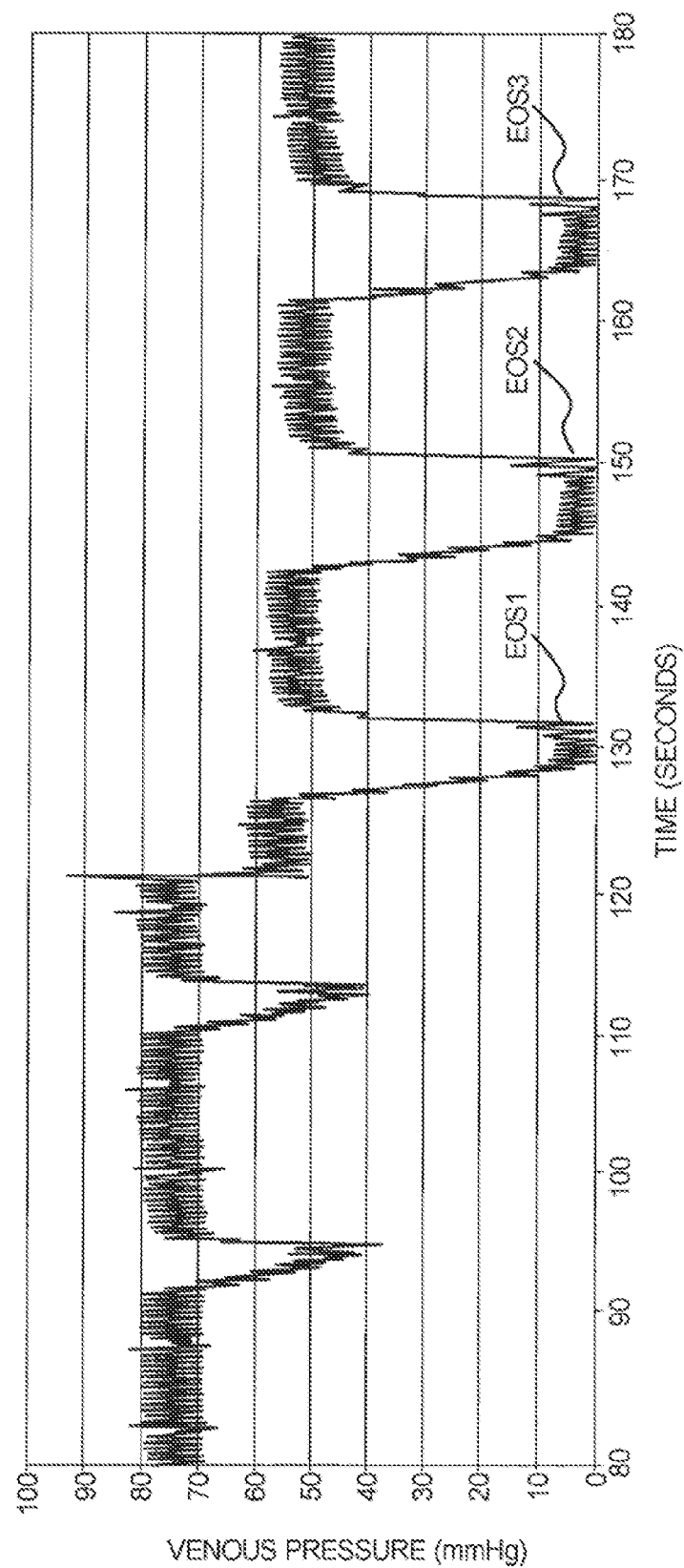
FIG. 7 is a graph illustrating the effect an access disconnection has on venous line pressure for another blood flowrate, patient venous access pressure and end-of-stroke time setting.

In FIG. 7, blood flowrate is reduced to 100 mL/min. In contrast to FIG. 6, which shows a large pressure spike upon needle dislodgment, FIG. 7 shows the dislodgement event occurring at approximately 120 seconds with a smaller spike in pressure. FIG. 7 shows that for a dislodgement at 100 mL/min blood flowrate, venous pressure at sensor 36a and during no-flow periods $T_{nf}$ drops from about 40 to 50 mmHg to about 0 to 7 mmHg (EOS 1 to 3). In FIG. 7, the increase in no-flow period is also readily evident after the dislodgement event (first primary embodiment).

Figure 8:
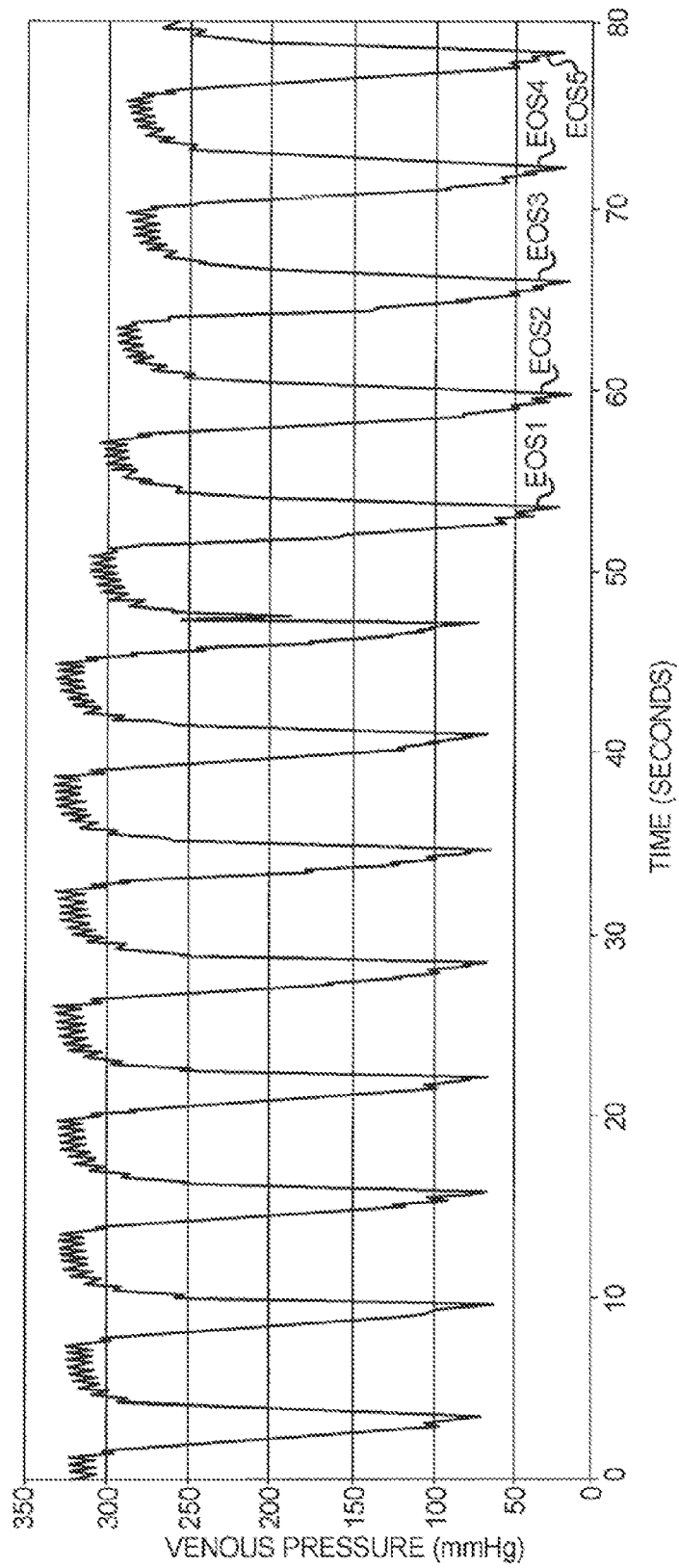
FIG. 8 is a graph illustrating the effect an access disconnection has on venous line pressure for a further blood flowrate, patient venous access pressure and end-of-stroke time setting.
Figure 9:
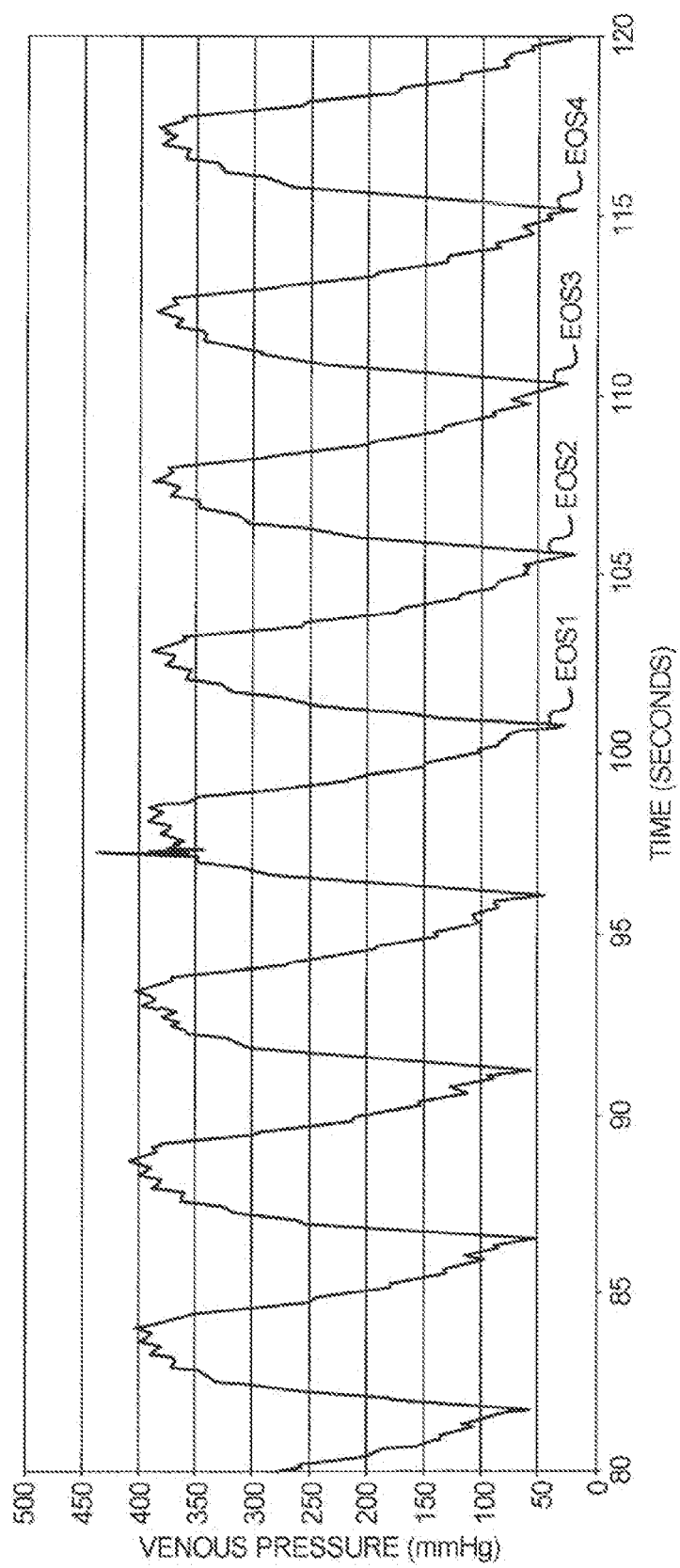
FIG. 9 is a graph illustrating the effect an access disconnection has on venous line pressure for a yet another blood flowrate, patient venous access pressure and end-of-stroke time setting.

FIGS. 8 and 9 show results for higher flowrates, namely, 300 mL/min and 400 mL/min, respectively. In FIG. 8 (300 mL/min), a dislodgement event occurs just prior to the time equal to fifty seconds. The venous pressure at sensor 36a and no-flow period $T_{nf}$ drops from about 75 mmHg to about 25 mmHg (see EOS 1 to 5). In FIG. 9 (400 mL/min), a dislodgement event occurs between ninety-five and one-hundred seconds. The venous pressure at sensor 36a and no-flow period $T_{nf}$ drops from about 45 to 60 mmHg to about 20 to 30 mmHg (see EOS 1 to 4). At the higher flowrates, the venous pressure measurement at the no-flow period $T_{nf}$ may need to be enhanced through the scheme described next, in which additional time is used to measure the venous pressure when a $T_{nf}$ venous pressure drop is first detected.

To make the effect at the higher flowrates more pronounced, it is contemplated to store an algorithm on logic implementer 100 that purposefully lengthens the no-flow period $T_{nf}$ through the control of diaphragm 28 via valves 24a to 24d, so that a truer venous pressure can be measured at sensor 36a during the no-flow periods. In FIG. 8, the no-flow periods $T_{nf}$ are controlled to be two seconds instead of one second. As is seen, the venous pressure measurement at sensor 36a and during no-flow periods $T_{nf}$ is more sensitive when the flow is allowed to decay more fully (compare EOS 1 to 3 of FIG. 8 to EOS 1 to 4 of FIG. 6).

Figure 10:
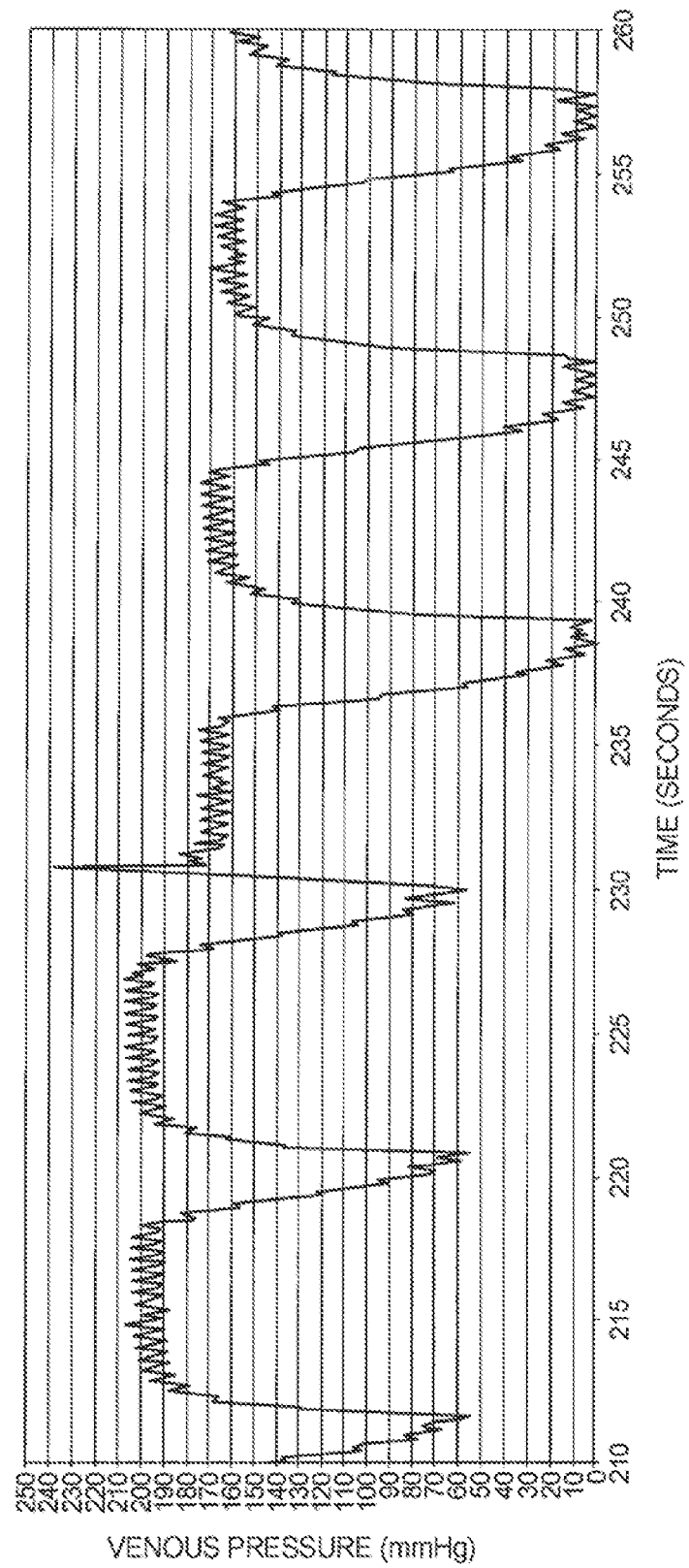
FIG. 10 is a graph illustrating the effect an access disconnection has on venous line pressure for still a further blood flowrate, patient venous access pressure and end-of-stroke time setting.

FIG. 10 shows that lengthening the no-flow periods $T_{nf}$ enables system 10 to make more representative measurements of the venous pressure during the no-flow periods $T_{nf}$ between diaphragm pumping cycles. It is contemplated therefore to program logic implementer 100 to monitor the venous pressure sensor 36a during a no-flow period $T_{nf}$ and upon sensing a dip in venous pressure, wait an additional period of time before moving diaphragm 28 to see how low the venous pressure might decay. This could be done for any length of no-flow period $T_{nf}$ only for short no-flow periods, e.g., one second or less. The logic implementer 100 could be further programmed to determine that an access disconnection has occurred during the additional no-flow period if the venous pressure decays past a predetermined threshold or a predetermined amount (delta).

It is contemplated to derive the predetermined pressure threshold or delta come from a pre-treatment assessment of the patient. When the access devices 16 and 20 are first inserted into patient 12 and there is no blood flowrate, system 10 senses and records the patient's base venous access pressure $P_{va}$ using sensor 36a. System 10 sets the predetermined threshold or delta using the sensed, steady state $P_{va}$ value. For example, if the patient's venous access pressure $P_{va}$ at steady state no-flow is fifty mmHg, a low threshold could be set to be 40 mmHg or the system could look for a delta change of ten mmHg Alternatively, if the patient's venous pressure during a long period of no-flow is fifty mmHg but upon the start of blood pumping, the no-flow pressure jumps to 60 mmHg, system 10 could be set for the blood flowrate to look for a delta or change in venous pressure of at least 20 mmHg Here, system 10 affords for natural changes in the patient's venous blood pressure (e.g., patient watches the ballgame during treatment and becomes excited) because the change in blood pressure should be reflected in the no-flow period $T_{nf}$ when venous needle 20 is lodged. To complete the example, system 10 would look for a change from, e.g., 80 mmHg no-flow venous pressure when the patient is excited to a 60 mmHg no-flow venous pressure for the given blood flowrate to determine that an access disconnection has occurred.

FIGS. 6, 8 and 9 do not show venous access pressure $P_{va}$ dropping to zero upon needle dislodgement. The reason for this is that the fluid path has compliance, namely, it stretches like a balloon. Even though the flow out of the blood pump has stopped for a short period, the balloon effect of the blood tubing causes a deflation of the tubing and flow accordingly continues during the EOS or no-flow period. Compliance is one reason to extend the EOS time when a $P_{va}$ drop is first detected. Extending the no-flow period can allow the blood tubing to deplete or constrict fully so that a truer patient venous access pressure $P_{va}$ can be detected.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis method comprising:
stopping a blood pump after pumping an amount of blood;
detecting a property indicative of whether a patient access device in fluid communication with the amount of blood is dislodged from the patient while the blood pump is stopped; and
determining whether the detected property indicates that the patient access device has been dislodged from the patient.

2. The dialysis method of claim 1, wherein if the determination is that the property indicates the patient access device has been dislodged from the patient, performing at least one of (i) shutting down the blood pump; (ii) clamping a blood line; and (iii) providing an alarm.

3. The dialysis method of claim 1, wherein detecting the property indicative of whether a patient access device is dislodged from the patient while the blood pump is stopped includes one of (i) measuring a pressure of blood in a flow path in communication with the patient access device and (ii) measuring a pressure of air used to drive the blood pump.

4. The dialysis method of claim 3, which includes determining that the property indicates that the patient access has been dislodged from the patient when the pressure measurement falls below a particular level.

5. The dialysis method of claim 1, wherein stopping the blood pump includes stopping a diaphragm of the blood pump from moving.

6. The dialysis method of claim 5, wherein detecting a property indicative of whether the patient access device is dislodged from the patient while the blood pump is stopped includes measuring a period in which the diaphragm is stopped.

7. The dialysis method of claim 6, wherein measuring the period in which the diaphragm is stopped includes measuring flow of blood through a flow path in communication with the patient access device.

8. The dialysis method of claim 6, wherein measuring the period in which the diaphragm is stopped includes measuring different time periods between different changes of pressure of blood through a flow path in communication with the patient access device.

9. The dialysis method of claim 6, which includes determining that the property indicates that the patient access device has been dislodged from the patient when the period in which the diaphragm is stopped extends past a particular duration.

10. The dialysis method of claim 1, wherein if the determination indicates that the patient access device has not been dislodged from the patient, re-actuating the blood pump.

11. The dialysis method of claim 1, wherein stopping the blood pump includes stopping a peristaltic pump roller or allowing a diaphragm of the blood pump to reach an end-of-stroke.

12. A dialysis method comprising:
- operating a blood pump to have a flow period and a no-flow period;
- in the no-flow period, detecting a first characteristic of a property when a patient access device is lodged in a patient, and detecting a second characteristic of the property when the patient access device is dislodged from the patient; and
- determining that the patient access device has been dislodged from the patient when the second characteristic of the property is detected.

13. The dialysis method of claim 12, wherein the property is time, the first characteristic is a shorter amount of time and the second characteristic is a longer amount of time.

14. The dialysis method of claim 12, wherein the property is blood pressure, the first characteristic being a higher blood pressure, the second characteristic being a lower blood pressure.

15. The dialysis method of claim 12, wherein the property is a first property, and which includes detecting a first characteristic of a second property when the patient access device is lodged in the patient and a second characteristic of the second property when the patient access device is dislodged from the patient, and which includes determining that the patient access device has been dislodged from the patient when the second characteristics of both the first and second properties are detected.

16. The dialysis method of claim 15, wherein the first property is time of the blood pump no-flow period, and the second property is a blood pressure during the blood pump no-flow period.

17. The dialysis method of claim 12, which includes lengthening the blood pump no-flow period, so as to enhance a difference between the first and second characteristics of the property.

18. A dialysis method comprising:
- storing a first characteristic of a property of a blood pump no-flow period that is indicative of a patient access device being lodged in a patient;
- storing a second characteristic of the property of the blood pump no-flow period that is indicative of the patient access device being dislodged from the patient, and
- determining that the patient access device being dislodged from the patient when the second characteristic of the property is detected.

19. The dialysis method of claim 18, wherein the property is time, the first characteristic is a shorter amount of time and the second characteristic is a longer amount of time.

20. The dialysis method of claim 18, wherein the property is blood pressure, the first characteristic being a higher blood pressure, the second characteristic being a lower blood pressure.

* * * * *